(12) United States Patent
Nesterenko et al.

(10) Patent No.: US 9,035,120 B2
(45) Date of Patent: May 19, 2015

(54) USE OF PHOSPHORUS MODIFIED MOLECULAR SIEVES IN CONVERSION OF ORGANICS TO OLEFINS

(75) Inventors: Nikolai Nesterenko, Nivelles (BE); Walter Vermeiren, Houthalen (BE); Delphine Minoux, Familleureux (BE); Sander Van Donk, Uccle (BE)

(73) Assignee: TOTAL RESEARCH & TECHNOLOGY FELUY, Seneffe (Feluy) (BE)

( * ) Notice: Subject to any disclaimer, the term of this patent is extended or adjusted under 35 U.S.C. 154(b) by 818 days.

(21) Appl. No.: 12/671,220

(22) PCT Filed: Jul. 28, 2008

(86) PCT No.: PCT/EP2008/059885
§ 371 (c)(1),
(2), (4) Date: Jun. 22, 2010

(87) PCT Pub. No.: WO2009/016155
PCT Pub. Date: Feb. 5, 2009

(65) Prior Publication Data
US 2010/0261944 A1    Oct. 14, 2010

(30) Foreign Application Priority Data

Jul. 31, 2007 (EP) .................................... 07113545
Jul. 31, 2007 (EP) .................................... 07113546
Sep. 12, 2007 (EP) .................................... 07116178

(51) Int. Cl.
| | | |
|---|---|---|
| C07C 1/00 | (2006.01) | |
| C07C 1/20 | (2006.01) | |
| B01J 29/40 | (2006.01) | |
| C07C 1/32 | (2006.01) | |
| C07C 4/06 | (2006.01) | |
| B01J 37/28 | (2006.01) | |

(52) U.S. Cl.
CPC . C07C 1/20 (2013.01); B01J 29/40 (2013.01); B01J 37/28 (2013.01); B01J 2229/18 (2013.01); B01J 2229/37 (2013.01); C07C 1/322 (2013.01); C07C 4/06 (2013.01); C10G 2400/20 (2013.01)

(58) Field of Classification Search
USPC ......... 585/324, 638, 639, 641, 648, 653, 640; 502/60, 73, 85, 78, 79
See application file for complete search history.

(56) References Cited

U.S. PATENT DOCUMENTS

| | | | |
|---|---|---|---|
| 3,911,041 A * | 10/1975 | Kaeding et al. ............... | 585/711 |
| 5,171,921 A | 12/1992 | Gaffney et al. | |
| 6,410,813 B1 | 6/2002 | Dath et al. | |
| 2003/0078463 A1 | 4/2003 | Martens et al. | |
| 2004/0102667 A1* | 5/2004 | Vora et al. ..................... | 585/324 |
| 2004/0254413 A1 | 12/2004 | Martens et al. | |
| 2005/0113517 A1* | 5/2005 | Tayano et al. ................. | 525/191 |
| 2006/0106270 A1 | 5/2006 | Glover et al. | |

OTHER PUBLICATIONS

Zhao Et al: "Effect of Phosphorus on HZSM-5 Catalyst for C4-oletin Cracking Reactions to Produce Propylene", Journal of Catalysis, Academic Press, Duluth, MN, US vol. 246, No. 1 (Apr. 23, 2007), pp. 29-37.

* cited by examiner

*Primary Examiner* — In Suk Bullock
*Assistant Examiner* — Sharon Pregler

(57) ABSTRACT

A method of making light olefins in a combined XTO (organics to olefins) and OCP (olefins cracking) process, from an oxygen-containing, halogenide-containing, or sulphur-containing organic feedstock contacted with a catalyst in a first reactor to convert the feedstock into a reactor effluent comprising light olefins and a heavy hydrocarbon fraction; separating the light olefins from the heavy hydrocarbon fraction, then contacting the heavy hydrocarbon fraction in a second reactor with a catalyst to convert a portion of the heavy hydrocarbons into light olefins; wherein the catalyst is a zeolite selected among a $H^+$ or $NH_4^+$—form of MFI, MEL, FER, MOR, or clinoptilolite; modifying the zeolite by adding from 0.05 to 7 wt % of phosphorous to the zeolite, and an optional washing and/or drying in either order, then calcination. In an embodiment, the initial zeolite Si:Al atomic ratio of at least one catalyst is 100 or less.

22 Claims, 3 Drawing Sheets

USE OF PHOSPHORUS MODIFIED MOLECULAR SIEVES IN CONVERSION OF ORGANICS TO OLEFINS

CROSS-REFERENCE TO RELATED APPLICATIONS

This application claims the benefit of PCT/EP2008/059885, filed Jul. 28, 2008, which claims the benefit of European Patent Application 07113546.1, filed on Jul. 31, 2007.

FIELD OF THE INVENTION

The present invention relates to an XTO (organics to olefins) process combined with an OCP (olefins cracking process) process based on phosphorus modified molecular sieves to make olefins. The limited supply and increasing cost of crude oil has prompted the search for alternative processes for producing hydrocarbon products. One such process is the conversion of oxygen-containing (by way of example methanol), halogenide-containing or sulphur-containing organic compounds to hydrocarbons and especially light olefins (by light olefins is meant $C_2$ to $C_4$ olefins) or gasoline and aromatics. In the present application the conversion of said oxygen-containing (also referred as oxygenates), halogenide-containing or sulphur-containing organic compounds to hydrocarbons and especially light olefins is referred as XTO process. The interest in the XTO process is based on the fact that feedstocks, especially methanol can be obtained from coal, hydrocarbon residues, biomass, organic waste or natural gas by the production of synthesis gas which is then processed to produce methanol. The XTO process can be combined with an OCP (olefins cracking process) process to increase production of olefins. The XTO process produces light olefins such as ethylene and propylene as well as heavy hydrocarbons such as butenes and above. These heavy hydrocarbons are cracked in an OCP process to give mainly ethylene and propylene.

BACKGROUND OF THE INVENTION

In accordance with U.S. Pat. No. 3,911,041, methanol or dimethyl ether is subjected to the action, at a temperature of at least about 300° C., with a catalyst comprising a crystalline aluminosilicate zeolite having a silica to alumina ratio of at least about 12, a constraint index of about 1 to 12, and containing phosphorus incorporated with the crystal structure thereof in an amount of at least about 0.78 percent by weight. The amount of the phosphorus incorporated with the crystal structure of the zeolite may be as high as about 4.5 percent by weight. The zeolite, preferably, also has a dried crystal density of not less than about 1.6 grams per cubic centimeter. The crystalline aluminosilicate zeolite having a silica to alumina ratio of at least about 12 is first converted to the hydrogen form, then phosphorus is introduced by reaction with a phosphorus-containing compound having a covalent or ionic constituent capable of reacting or exchanging with hydrogen ion and thereafter heating. There is no steaming of the zeolite prior to introduction of phosphorus. Preferably, prior to reacting the zeolite with the phosphorus-containing compound, the zeolite is dried. Drying can be effected in the presence of air. Elevated temperatures may be employed. There is no combination with an OCP process.

In accordance with U.S. Pat. No. 5,573,990 methanol and/or dimethylether is converted in presence of a catalyst which contains at least 0.7% by weight of phosphorus and at least 0.97% by weight of rare earth elements incorporated within the structure of the catalyst. Preferably the amount of phosphorus is comprised between 0.7 and 5% by weight. The phosphorus content in the catalyst is most preferably comprised between 1.3 and 1.7% by weight. The rare earth elements incorporated with the crystal structure of the catalyst are preferably rich in lanthanum, the content of lanthanum in the catalyst being preferably comprised between 2.5 and 3.5% by weight. The zeolite ZSM-5 based catalyst presents a mole ratio $SiO_2/Al_2O_3$ comprised between 40 and 80, a crystal size comprised between 1 and 10 μm and adsorption capacities of n-hexane and water 10-11% by weight and 6-7% by weight respectively. Said ZSM-5 is synthesized in the presence of a template, then is converted to the hydrogen form by ion exchange with hydrochloric acid. The zeolite HZSM-5 prepared as described above is impregnated in aqueous phosphoric acid solution under reduced pressure preferably comprised between 0.08 and 0.09 MPa for 2-3 hours. It is dried at <110° C. for 3-5 hours and calcined at about 540° C. for about 3 hours, the phosphorus content of the obtained product PZSM-5 being 0.7-5% (by weight). There is no steaming of the zeolite prior to introduction of phosphorus. The feedstock methanol comprises steam in a ratio methanol/steam 10-50/90-50, the examples are made with a ratio 30/70. There is no combination with an OCP process.

U.S. Pat. No. 6,797,851 uses at least two different zeolite catalysts to produce an olefin composition from an oxygenate, for example, two different ZSM-type catalysts, to produce olefin having a significant quantity of ethylene and propylene. The catalysts can be mixed together in one reactor, arranged in separate beds, or used in separate reactors in series. It is desirable that one of the zeolite catalysts contains a ZSM-5 molecular sieve. The ZSM-5 molecular sieve is selected from the group consisting of an unmodified ZSM-5, a phosphorous modified ZSM-5, a steam modified ZSM-5 having a micropore volume reduced to not less than 50% of that of the unsteamed ZSM-5, and mixtures thereof. It is also desirable to have a second zeolite catalyst which contains a zeolite molecular sieve selected from the group consisting of 10-ring zeolites such as ZSM-22, ZSM-23, ZSM-35, ZSM-48, and a mixture thereof. In one embodiment, the zeolite employed in the first stage of the above process is ZSM-5 having a silica to alumina molar ratio of at least 250, as measured prior to any treatment of the zeolite to adjust its diffusivity. According to one embodiment, the zeolite is modified with a phosphorous containing compound to control reduction in pore volume. Alternatively, the zeolite is steamed, and the phosphorous compound is added prior to or after steaming. After contacting with the phosphorus-containing compound, the porous crystalline material, according to one embodiment, is dried and calcined to convert the phosphorus to an oxide form. One or more inert diluents may be present in the oxygenate feedstock. Preferred diluents are water and nitrogen. Water can be injected in either liquid or vapor form. For example, the process may be conducted in the presence of water such that the molar ratio water to methanol in the feed is from about 0.01:1 to about 10:1. According to FIG. 2 the conversion of methanol leads to a mixture of light olefins and a C4+ olefin stream, Said C4+ olefin stream is sent to a fixed bed containing ZSM-22 or ZSM-35 to produce additional ethylene and propylene. These ZSM-22 or ZSM-35 are not P-modified.

US20060106270A1 relates to a process wherein the average propylene cycle selectivity of an oxygenate to propylene (OTP) process using a dual-function oxygenate conversion catalyst is substantially enhanced by the use of a combination of: 1) moving bed reactor technology in the hydrocarbon synthesis portion of the OTP flow scheme in lieu of the fixed bed technology of the prior art; 2) a hydrothermally stabilized and dual-functional catalyst system comprising a molecular sieve having dual-function capability dispersed in a phosphorus-modified alumina matrix containing labile phosphorus and/or aluminum anions; and 3) a catalyst on-stream cycle time of 400 hours or less. The use of a mixture of a zeolitic catalyst system with a non-zeolitic catalyst system is described. This mixed catalyst embodiment can be accomplished either using a physical mixture of particles containing the zeolitic material with particles containing the non-zeolitic material or the catalyst can be formulated by mixing the two types of material into the phosphorus modified aluminum matrix in order to form particles having both ingredients present therein. In either case the preferred combination is a mixture of ZSM-5 or ZSM-11 with SAPO-34 in relative amounts such that ZSM-5 or ZSM-11 comprises 30 to 95 wt % of the molecular sieve portion of the mixture with a value of about 50 to 90 wt % being especially preferred. It doesn't describe phosphorus modified molecular sieves. A diluent is preferably used in order to control partial pressure of the oxygenate reactant in the OTP conversion zone and in order to shift the overall reaction selectivity towards propylene. An especially preferred diluent for use is steam since it is relatively easily recovered from the product effluent stream utilizing condensation techniques. The amount of diluent used will be selected from the range from about 0.1:1 to 5:1 moles of diluent per mole of oxygenate and preferably 0.5:1 to 2:1 in order to lower the partial pressure of the oxygenates to a level which favors production of propylene. There is no combination with an OCP process.

EP448000 relates to a process for the conversion of methanol or dimethylether into light olefins in presence of water vapour over a silicoaluminate of the pentasil structure of at least Si/Al ratio of 10, producing at least 5 wt % of ethylene, at least 35 wt % of propylene and at most 30 wt % butenes by (1) using a total pressure of 10 to 90 kPa, (2) a weight ratio of water to methanol of 0.1 to 1.5, (3) a reactor temperature of 280 to 570° C. and (4) a proton-containing catalyst of the pentasil-type, having an alkali-content of at most 380 ppm, less than 0.1 wt % of ZnO and less than 0.1 wt % of CdO and a BET surface area of 300 to 600 m2/gram and a pore volume of 0.3 to 0.8 cm3/gram. There is no combination with an OCP process.

It has been discovered that the use of a P-modified zeolite in the XTO reactor and in the OCP reactor has many advantages.

The phosphorus modified molecular sieves of the present invention is prepared based on MFI, MOR, MEL, clinoptilolite or FER crystalline aluminosilicate molecular sieves having an initial Si/Al ratio advantageously between 4 and 500.

The P-modified zeolites of this recipe can be obtained based on cheap crystalline alumosilicates with low Si/Al ratio (below 30). This provides a lower final catalyst cost. The catalysts show high C3-yield, high C3-/C2-ratio, high stability, high C3's purity and reduced selectivity to paraffin's and to aromatic in XTO. These catalysts provide also the additional flexibility for ethylene and C4+ recycling for additional propylene production. The average propylene yield can be substantially enhanced by using these catalysts in a combination of XTO and OCP process.

BRIEF DESCRIPTION OF THE INVENTION

The present invention relates to a process to make light olefins, in a combined XTO-OCP process, from an oxygen-containing, halogenide-containing or sulphur-containing organic feedstock comprising:

contacting said oxygen-containing, halogenide-containing or sulphur-containing organic feedstock in the XTO reactor with a catalyst made of a P-modified zeolite (A) at conditions effective to convert at least a portion of the feedstock to form a XTO reactor effluent comprising light olefins and a heavy hydrocarbon fraction;

separating said light olefins from said heavy hydrocarbon fraction;

contacting said heavy hydrocarbon fraction in the OCP reactor with a catalyst made of a P-modified zeolite (A) at conditions effective to convert at least a portion of said heavy hydrocarbon fraction to light olefins;

wherein said P-modified zeolite (A) is made by a process comprising in that order:
  selecting a zeolite (advantageously with Si/Al ratio between 4 and 500) among $H^+$ or $NH_4^+$-form of MFI, MEL, FER, MOR, clinoptilolite;
  introducing P at conditions effective to introduce advantageously at least 0.05 wt % of P;
  separation of the solid from the liquid if any;
  an optional washing step or an optional drying step or an optional drying step followed by a washing step;
  a calcination step; the catalyst of the XTO and the catalyst of the OCP being the same or different.

It is desirable to have a substantially 100% conversion of the organic compound in the XTO reactor. This conversion rate is adjusted by optimization of contact time and the frequency of regeneration of the catalyst.

The XTO reactor and the OCP reactor are separate reaction zones.

The zeolite with low Si/Al ratio has been made previously with or without direct addition of an organic template.

Optionally the process to make (A) comprises the steps of steaming and leaching. The method consists in steaming followed by leaching. It is generally known by the persons in the art that steam treatment of zeolites, results in aluminium that leaves the zeolite framework and resides as aluminiumoxides in and outside the pores of the zeolite. This transformation is known as dealumination of zeolites and this term will be used throughout the text. The treatment of the steamed zeolite with an acid solution results in dissolution of the extra-framework aluminiumoxides. This transformation is known as leaching and this term will be used throughout the text. Then the zeolite is separated, advantageously by filtration, and optionally washed. A drying step can be envisaged between filtering and washing steps. The solution after the washing can be either separated, by way of example, by filtering from the solid or evaporated.

P can be introduced by any means or, by way of example, according to the recipe described in U.S. Pat. No. 3,911,041, U.S. Pat. No. 5,573,990 and U.S. Pat. No. 6,797,851.

With regards to said effluent of the XTO process, "light olefins" means ethylene and propylene and the "heavy hydrocarbon fraction" is defined herein as the fraction containing hydrocarbons having a molecular weight greater than propane, which means hydrocarbons having 4 carbon atoms or more and written as $C_4^+$.

The catalyst made of a P-modified zeolite (A) can be the P-modified zeolite (A) itself or it can be the P-modified zeolite (A) formulated into a catalyst by combining with other materials that provide additional hardness or catalytic activity to the finished catalyst product.

The catalyst of the XTO reactor and of the OCP reactor can be the same or different but comprised in the same above description. By way of example the XTO catalyst can be based on a zeolite and the OCP catalyst can be based on a different zeolite or the same zeolite with a different P content or a different Si/Al ratio or any combination thereof.

The separation of the liquid from the solid is advantageously made by filtering at a temperature between 0-90° C., centrifugation at a temperature between 0-90° C., evaporation or equivalent.

Optionally, the zeolite can be dried after separation before washing. Advantageously said drying is made at a temperature between 40-600° C., advantageously for 1-10 h. This drying can be processed either in a static condition or in a gas flow. Air, nitrogen or any inert gases can be used.

The washing step can be performed either during the filtering (separation step) with a portion of cold (<40° C.) or hot water (>40 but <90° C.) or the solid can be subjected to a water solution (1 kg of solid/4 liters water solution) and treated under reflux conditions for 0.5-10 h followed by evaporation or filtering.

Final calcination step is performed advantageously at the temperature 400-700° C. either in a static condition or in a gas flow. Air, nitrogen or any inert gases can be used.

According to an embodiment of the invention the phosphorous modified zeolite (A) is made by a process comprising in that order:
- selecting a zeolite (advantageously with Si/Al ratio between 4 and 500, from 4 to 30 in a specific embodiment) among $H^+$ or $NH_4^+$-form of MFI, MEL, FER, MOR, clinoptilolite;
- steaming at a temperature ranging from 400 to 870° C. for 0.01-200 h;
- leaching with an aqueous acid solution at conditions effective to remove a substantial part of Al from the zeolite;
- introducing P with an aqueous solution containing the source of P at conditions effective to introduce advantageously at least 0.05 wt % of P;
- separation of the solid from the liquid;
- an optional washing step or an optional drying step or an optional drying step followed by a washing step;
- a calcination step.

Optionally between the steaming step and the leaching step there is an intermediate step such as, by way of example, contact with silica powder and drying.

DETAILED DESCRIPTION OF THE INVENTION

Figure 1:
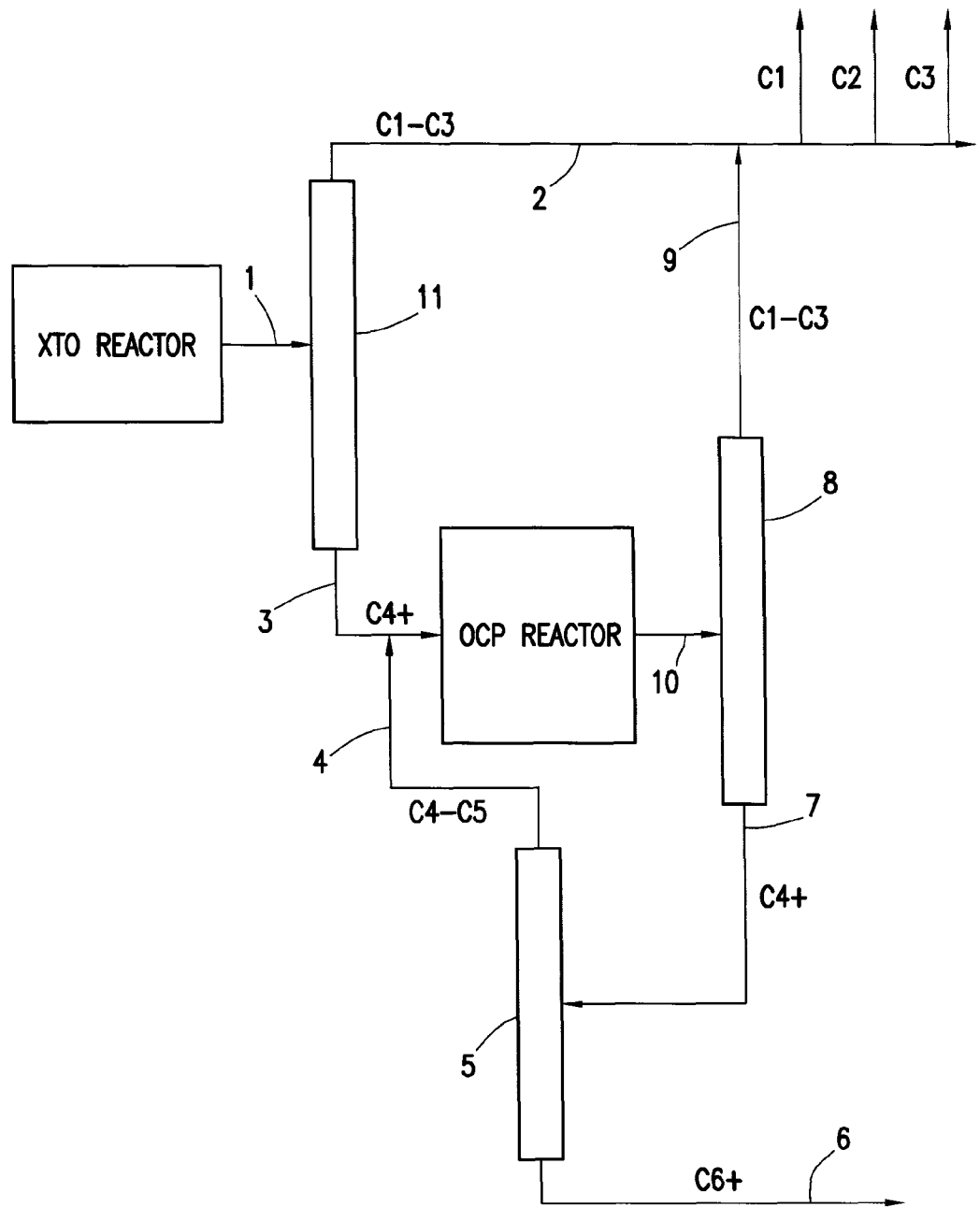
FIG. 1 illustrates a specific embodiment of the invention and is a schematic of a series of reactors and fractionators for carrying out a process of the invention, and also illustrates features of recycling in certain aspects of the embodiment.

As regards (A) and the selected zeolite, advantageously it is a crystalline alumosilicate of the MFI family or the MEL family. An example of MFI silicates is ZSM-5. An example of an MEL zeolite is ZSM-11 which is known in the art. Other examples are described by the International Zeolite Association (*Atlas of Zeolite Structure Types*, 1987, Butterworths).

Crystalline silicates are microporous crystalline inorganic polymers based on a framework of $XO_4$ tetrahydra linked to each other by sharing of oxygen ions, where X may be trivalent (e.g. Al, B, ...) or tetravalent (e.g. Ge, Si, ...). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline alumosilicates are similar in size to many organic molecules of practical interest, they control the ingress and egress of reactants and products, resulting in particular selectivity in catalytic reactions. Crystalline alumosilicates with the MFI structure possess a bi-directional intersecting pore system with the following pore diameters: a straight channel along [010]: 0.53-0.56 nm and a sinusoidal channel along [100]: 0.51-0.55 nm. Crystalline alumosilicates with the MEL structure possess a bi-directional intersecting straight pore system with straight channels along [100] having pore diameters of 0.53-0.54 nm.

Advantageously the selected MFI, MEL, FER, MOR, clinoptilolite (or $H^+$ or $NH_4^+$-form MFI, MEL, FER, MOR, clinoptilolite) has an initial atomic ratio Si/Al of 100 or lower and from 4 to 30 in a specific embodiment. The conversion to the $H^+$ or $NH_4^+$-form is known per se and is described in U.S. Pat. No. 3,911,041 and U.S. Pat. No. 5,573,990.

Advantageously the final P-content of (A) is at least 0.05 wt % and preferably between 0.3 and 7 w %. Advantageously at least 10% of Al, in respect to parent zeolite MFI, MEL, FER, MOR and clinoptilolite, have been extracted and removed from the zeolite by the leaching.

Then the zeolite either is separated from the washing solution or is dried without separation from the washing solution. Said separation is advantageously made by filtration. Then the zeolite is calcined, by way of example, at 400° C. for 2-10 hours.

In the steam treatment step, the temperature is preferably from 420 to 870° C., more preferably from 480 to 760° C. The pressure is preferably atmospheric pressure and the water partial pressure may range from 13 to 100 kPa. The steam atmosphere preferably contains from 5 to 100 vol % steam with from 0 to 95 vol % of an inert gas, preferably nitrogen. The steam treatment is preferably carried out for a period of from 0.01 to 200 hours, advantageously from 0.05 to 200 hours, more preferably from 0.05 to 50 hours. The steam treatment tends to reduce the amount of tetrahedral aluminium in the crystalline silicate framework by forming alumina.

The leaching can be made with an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, phosphoric acid, phosphonic acid, sulfuric acid or a salt of such an acid (e.g. the sodium or ammonium salts) or a mixture of two or more of such acids or salts.

The residual P-content is adjusted by P-concentration in the aqueous acid solution containing the source of P, drying conditions and a washing procedure if any. A drying step can be envisaged between filtering and washing steps.

The solid (A) can be used as itself as a catalyst. In another embodiment it can be formulated into a catalyst by combining with other materials that provide additional hardness or catalytic activity to the finished catalyst product. Materials which can be blended with (A) can be various inert or catalytically active materials, or various binder materials. These materials include compositions such as kaolin and other clays, various forms of rare earth metals, phosphates, alumina or alumina sol, titania, zirconia, quartz, silica or silica sol, and mixtures thereof. These components are effective in densifying the catalyst and increasing the strength of the formulated catalyst. The catalyst may be formulated into pellets, spheres, extruded into other shapes, or formed into a spray-dried particles. The amount of (A) which is contained in the final catalyst product ranges from 10 to 90 weight percent of the total catalyst, preferably 20 to 70 weight percent of the total catalyst.

With regards to the XTO process, the catalyst of the invention is particularly suited for the catalytic conversion of oxygen-containing, halogenide-containing or sulphur-containing organic compounds to hydrocarbons.

In this process a feedstock containing an oxygen-containing, halogenide-containing or sulphur-containing organic compound contacts the above described catalyst in a reaction zone of a reactor at conditions effective to produce light olefins, particularly ethylene and propylene. Typically, the oxygen-containing, halogenide-containing or sulphur-containing organic feedstock is contacted with the catalyst when the oxygen-containing, halogenide-containing or sulphur-containing organic compounds is in vapour phase. Alternately, the process may be carried out in a liquid or a mixed vapour/liquid phase. In this process, converting oxygen-containing, halogenide-containing or sulphur-containing organic compounds, olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of at least 300° C., and up to 600° C. is preferred.

The pressure also may vary over a wide range. Preferred pressures are in the range of about 5 kPa to about 5 MPa, with the most preferred range being of from about 50 kPa to about 0.5 MPa. The foregoing pressures refer to the partial pressure of the oxygen-containing, halogenide-containing, sulphur-containing organic compounds and/or mixtures thereof.

The process can be carried out in any system using a variety of transport beds, although a fixed bed or moving bed system could be used. Advantageously a fluidized bed is used. It is particularly desirable to operate the reaction process at high space velocities. The process can be conducted in a single reaction zone or a number of reaction zones arranged in series or in parallel. Any standard commercial scale reactor system can be used, for example fixed bed, fluidised or moving bed systems. After a certain time on—stream the catalyst needs to be regenerated. This regeneration can be carried out in a separate reactor or in the same reactor. In case of a moving bed or fluidised bed reactor, a part of the catalyst is continuously or intermittently withdrawn from the conversion reactor and sent to a second reactor for regeneration. After the regeneration, the regenerated catalyst is continuously or intermittently sent back to the conversion reactor. In case of fixed bed reactor the reactor is taken off-line for regeneration. Generally this requires a second spare reactor that can take over the conversion into light olefins. After regeneration the fixed bed reactor is in stand-by until the spare reactor needs regeneration and the regenerated reactor takes over the conversion. Regeneration is carried out by injecting an oxygen-containing stream over the catalyst at sufficient high temperature to burn the deposited coke on the catalyst. The commercial scale reactor systems can be operated at a weight hourly space velocity (WHSV) of from 0.1 hr$^{-1}$ to 1000 hr$^{-1}$.

One or more inert diluents may be present in the feedstock, for example, in an amount of from 1 to 95 molar percent, based on the total number of moles of all feed and diluent components fed to the reaction zone. Typical diluents include, but are not necessarily limited to, helium, argon, nitrogen, carbon monoxide, carbon dioxide, hydrogen, water, paraffins, alkanes (especially methane, ethane, and propane), aromatic compounds, and mixtures thereof. The preferred diluents are water and nitrogen. Water can be injected in either liquid or vapour form.

According to a specific embodiment essentially no water (or steam) is injected as diluent of the feedstock sent to the XTO reactor. However it means that the feedstock can contain the water already contained in the fresh oxygen-containing, halogenide-containing or sulphur-containing organic feedstock or the steam used to engage the proper flowing and purging of catalyst in transport or moving bed reactors of the XTO reactor.

The oxygenate feedstock is any feedstock containing a molecule or any chemical having at least an oxygen atom and capable, in the presence of the above catalyst, to be converted to olefin products. The oxygenate feedstock comprises at least one organic compound which contains at least one oxygen atom, such as aliphatic alcohols, ethers, carbonyl compounds (aldehydes, ketones, carboxylic acids, carbonates, esters and the like). Representative oxygenates include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Representative oxygenates include lower straight chain or branched aliphatic alcohols, their unsaturated counterparts. Analogously to these oxygenates, compounds containing sulphur or halides may be used. Examples of suitable compounds include methyl mercaptan; dimethyl sulfide; ethyl mercaptan; di-ethyl sulfide; ethyl monochloride; methyl monochloride, methyl dichloride, n-alkyl halides, n-alkyl sulfides having n-alkyl groups of comprising the range of from about 1 to about 10 carbon atoms; and mixtures thereof. Preferred oxygenate compounds are methanol, dimethyl ether, or a mixture thereof.

In XTO effluent among the olefins having 4 carbon atoms or more there are more than 50 weight % of butenes.

With regards to said effluent of the XTO process, "light olefins" means ethylene and propylene and the "heavy hydrocarbon fraction" is defined herein as the fraction containing hydrocarbons having a molecular weight greater than propane, which means hydrocarbons having 4 carbon atoms or more and written as $C_4^+$.

With regards to the OCP process, said process is known per se. It has been described in EP 1036133, EP 1035915, EP 1036134, EP 1036135, EP 1036136, EP 1036138, EP 1036137, EP 1036139, EP 1194502, EP 1190015, EP 1194500 and EP 1363983 the content of which are incorporated in the present invention. The heavy hydrocarbon fraction produced in the XTO reactor is converted in the OCP reactor, also called an "olefin cracking reactor" herein, to produce additional amounts of ethylene and propylene.

The catalysts found to produce this conversion are the catalysts consisting of the above (A) or comprising the above (A). They can be the same as the catalysts of the XTO reactor or although they are in the description of (A) they can be different of the XTO catalyst because of the starting zeolite, the P content etc. . . .

The crystalline alumosilicate catalyst has structural and chemical properties and is employed under particular reaction conditions whereby the catalytic cracking of the $C_4^+$ olefins readily proceeds. Different reaction pathways can occur on the catalyst. Under the process conditions, having an inlet temperature of around 400° to 600° C., preferably from 520° to 600° C., yet more preferably 540° to 580° C., and an olefin partial pressure of from 0.1 to 2 bars, most preferably around atmospheric pressure. Olefinic catalytic cracking may be understood to comprise a process yielding shorter molecules via bond breakage.

In the catalytic cracking process of the OCP reactor, the process conditions are selected in order to provide high selectivity towards propylene or ethylene, as desired, a stable olefin conversion over time, and a stable olefinic product distribution in the effluent. Such objectives are favoured with a low pressure, a high inlet temperature and a short contact time, all of which process parameters are interrelated and provide an overall cumulative effect.

The process conditions are selected to disfavour hydrogen transfer reactions leading to the formation of paraffins, aromatics and coke precursors. The process operating conditions thus employ a high space velocity, a low pressure and a high reaction temperature. The LHSV ranges from 0.5 to 30 $hr^{-1}$, preferably from 1 to 30 $hr^{-1}$. The olefin partial pressure ranges from 0.1 to 2 bars, preferably from 0.5 to 1.5 bars (absolute pressures referred to herein). A particularly preferred olefin partial pressure is atmospheric pressure (i.e. 1 bar). The heavy hydrocarbon fraction feedstock is preferably fed at a total inlet pressure sufficient to convey the feedstocks through the reactor. Said feedstock may be fed undiluted or diluted in an inert gas, e.g. nitrogen or steam. Preferably, the total absolute pressure in the second reactor ranges from 0.5 to 10 bars. The use of a low olefin partial pressure, for example atmospheric pressure, tends to lower the incidence of hydrogen transfer reactions in the cracking process, which in turn reduces the potential for coke formation which tends to reduce catalyst stability. The cracking of the olefins is preferably performed at an inlet temperature of the feedstock of from 400° to 650° C., more preferably from 450° to 600° C., yet more preferably from 540° C. to 590° C.

In order to maximize the amount of ethylene and propylene and to minimize the production of methane, aromatics and coke, it is desired to minimize the presence of diolefins in the feed. Diolefin conversion to monoolefin hydrocarbons may be accomplished with a conventional selective hydrogenation process such as disclosed in U.S. Pat. No. 4,695,560 hereby incorporated by reference.

The OCP reactor can be a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. As described above, the process may be performed continuously using a pair of parallel "swing" reactors. The heavy hydrocarbon fraction cracking process is endothermic; therefore, the reactor should be adapted to supply heat as necessary to maintain a suitable reaction temperature. Online or periodic regeneration of the catalyst may be provided by any suitable means known in the art.

The various preferred catalysts of the OCP reactor have been found to exhibit high stability, in particular being capable of giving a stable propylene yield over several days, e.g. up to ten days. This enables the olefin cracking process to be performed continuously in two parallel "swing" reactors wherein when one reactor is in operation, the other reactor is undergoing catalyst regeneration. The catalyst can be regenerated several times.

The OCP reactor effluent comprises methane, light olefins and hydrocarbons having 4 carbon atoms or more. Advantageously said OCP reactor effluent is sent to a fractionator and the light olefins are recovered. Advantageously the hydrocarbons having 4 carbon atoms or more are recycled at the inlet of the OCP reactor, optionally mixed with the heavy hydrocarbon recovered from the effluent of the XTO reactor. Advantageously, before recycling said hydrocarbons having 4 carbon atoms or more at the inlet of the OCP reactor, said hydrocarbons having 4 carbon atoms or more are sent to a second fractionator to purge the heavies. In a preferred embodiment the light olefins recovered from the effluent of the XTO reactor and the light olefins recovered from the fractionator following the OCP reactor are treated in a common recovery section.

Optionally, in order to adjust the propylene to ethylene ratio of the whole process (XTO+OCP), ethylene in whole or in part can be recycled over the OCP reactor and advantageously converted into more propylene. This ethylene can either come from the fractionation section of the XTO reactor or from the fractionation section of the OCP reactor or from both the fractionation section of the XTO reactor and the fractionation section of the OCP reactor or even from the optional common recovery section.

Optionally, in order to adjust the propylene to ethylene ratio of the whole process (XTO+OCP), ethylene in whole or in part can be recycled over the XTO reactor where it combines with the oxygen-containing, halogenide-containing or sulphur-containing organic feedstock to form more propylene. This ethylene can either come from the fractionation section of the XTO reactor or from the fractionation section of the OCP reactor or from both the fractionation section of the XTO reactor and the fraction section of the OCP reactor or even from the optional common recovery section.

These ways of operation allow to respond with the same equipment and catalyst to market propylene to ethylene demand.

FIG. 1 illustrates a specific embodiment of the invention. The effluent of the XTO reactor 1 is passed to a fractionator 11. The overhead, a C1-C3 fraction including the light olefins is sent via line 2 to a common recovery section (not shown). The bottoms (the heavy hydrocarbon fraction) are sent via line 3 to the OCP reactor. The effluent of the OCP reactor is sent via line 10 to a fractionator 8. The overhead, a C1-C3 fraction including the light olefins, is sent via line 9 to a common recovery section (not shown). The bottoms, hydrocarbons having 4 carbon atoms or more, are sent to a fractionator 5. The overhead, hydrocarbons having 4 to substantially 5 carbon atoms are recycled via line 4 to the inlet of the OCP reactor. The bottoms, hydrocarbons having substantially 6 carbon atoms or more, are purged via line 6.

The method of making the olefin products from an oxygenate feedstock can include the additional step of making the oxygenate feedstock from hydrocarbons such as oil, coal, tar sand, shale, biomass and natural gas. Methods for making oxygenate feedstocks are known in the art. These methods include fermentation to alcohol or ether, making synthesis gas, then converting the synthesis gas to alcohol or ether. Synthesis gas can be produced by known processes such as steam reforming, autothermal reforming and partial oxidization in case of gas feedstocks or by reforming or gasification using oxygen and steam in case of solid (coal, organic waste) or liquid feedstocks. Methanol, methylsulfide and methylhalides can be produced by oxidation of methane with the help of dioxygen, sulphur or halides in the corresponding oxygen-containing, halogenide-containing or sulphur-containing organic compound.

One skilled in the art will also appreciate that the olefin products made by the oxygenate-to-olefin conversion reaction using the molecular sieve of the present invention can be polymerized optionally with one or more comonomers to form polyolefins, particularly polyethylenes and polypropylenes. The present invention relates also to said polyethylenes and polypropylenes.

EXAMPLES

Example 1

A sample of zeolite ZSM-5 with Si/Al=13 in H-form synthesized without template has been obtained from TRICAT (TZP-302).

Example 2

The sample from example 1 was steamed at 550° C. for 48 h. Then the steamed solid was treated with 3.14M solution of $H_3PO4$ for 18 h under reflux condition (4.2 liter/1 kg of zeolite). Then the solid was separated by filtering from the solution. Obtained solid was dried at 110° C. for 16 h and calcined at 400° C. for 10 h. (Atomic ratio Si/Al 25, P-content 5.6 wt %).

The sample is hereinafter identified as Sample A.

Example 3

The sample from example 1 was directly treated with 3.14M solution of $H_3PO4$ for 18 h under reflux condition (4.2 liter/1 kg of zeolite). Then the solid was separated by filtering from the solution. (Atomic ratio Si/Al— 15.5, P-content 0.33 wt %). Obtained solid was dried at 110° C. for 16 h and calcined at 400° C. for 10 h.

The sample is hereinafter identified as Sample B.

Example 4

A sample of silicalite S-115 with atomic ratio Si/Al=150 has been obtained from UOP. The sample was steamed at 550° C. for 48 h and exchanged with 0.104M $H_3PO_4$ for 18 h under reflux condition (4.2 liter/1 kg of zeolite). Obtained solid was dried at 110° C. for 16 h and calcined at 400° C. for 10 h. (Atomic ratio Si/Al— 260, P-content 0.11 wt %).

The sample is hereinafter identified as Sample C.

Example 5

A sample of zeolite ZSM-5 with Si/Al=21 in $NH_4$-form has been obtained from PQ Corporation (CBV 5020). The sample was calcined at 550° C. for 6 h. 20 g of the calcined zeolite was impregnated with a solution containing 16.7 g water and 4.26 g $(NH_4)_2HPO_4$. Finally the P-zeolite was dried overnight at 110° C. and calcined at 600° C. for 10 h. (Atomic ratio Si/Al 21, P-content 3.5 wt %).

The sample is hereinafter identified as Sample D.

Example 6

A sample of zeolite ZSM-5 with Si/Al=21 in $NH_4$-form has been obtained from PQ Corporation (CBV 5020). The sample was steamed at 680° C. for 4 h. The steamed solid was treated by 3.14M solution of $H_3PO4$ for 18 h under reflux condition (4.2 liter/1 kg of zeolite). Then the solid was separated by filtering from the solution and washed with 2000 ml of distilled water per kg of zeolite. (Atomic ratio Si/Al 50, P-content 1.2 wt %). Finally the P-zeolite was dried overnight at 110° C. and calcined at 600° C. for 10 h.

The sample is hereinafter identified as Sample E.

Example 7

A sample of zeolite ZSM-5 with Si/Al=38 in $NH_4$-form has been obtained from Zeolyst International (CBV 8054). The sample was calcined at 550° C. for 6 h. 20 g of the calcined zeolite was impregnated with a solution containing 16.2 g water and 1.707 g $(NH_4)_2HPO_4$. (Atomic ratio Si/Al 38, P-content 1.75 wt %). Finally the P-zeolite was dried overnight at 110° C. and calcined at 600° C. for 10 h.

The sample is hereinafter identified as Sample G.

Example 8

XTO Conditions (XTO in the Table)

Catalyst tests were performed on 2 g catalyst samples with a pure methanol feed in a fixed-bed, down flow stainless-steel reactor. Catalyst powders was pressed into wafers and crushed to 35-45 mesh particles. Prior to catalytic run all catalysts were heated in flowing $N_2$ (5 Nl/h) up to the reaction temperature. Analysis of the products has been performed on-line by a gas chromatograph equipped with a capillary column. The catalytic performance is given at full methanol conversion and maximum propylene yield. The results are displayed on carbon and water free basis. The values in table 1 are the weight percent on carbon basis. The table gives also the $C_4$+ olefins produced over the XTO catalyst that can be used for further conversion over the OCP catalyst.

TABLE 1

|  | Sample A P-ZSM-5 | Sample D P-ZSM-5 | Sample E P-ZSM-5 | Sample G P-ZSM-5 |
|---|---|---|---|---|
| Si/Al | 25 | 21 | 50 | 39 |
| P, % | 5.6 | 3.5 | 1.2 | 1.75 |
| XTO |  |  |  |  |
| T, ° C. | 550 | 550 | 550 | 550 |
| WHSV. h-1 | 1.6 | 1.6 | 1.6 | 1.6 |
| P, barg | 0.5 | 0.5 | 0.5 | 0.5 |
| C1 (methane) | 1.6 | 1.6 | 1.6 | 1.9 |
| Paraffins | 5.5 | 5.5 | 5.0 | 4.5 |
| Olefins | 86.1 | 87.6 | 87.1 | 85.0 |
| Dienes | 1.9 | 1.7 | 1.9 | 1.4 |
| Aromatics | 5.2 | 4.2 | 4.3 | 7.7 |
| C3−/C2− | 4.8 | 3.8 | 6.3 | 4.2 |
| C2− + C3− | 46 | 48 | 44 | 47 |
| ethylene | 8 | 10 | 6 | 9 |
| propylene | 38 | 38 | 38 | 38 |
| OCP feed (Non cyclic olefins $C_4$+) |  |  |  |  |
| Σ olefins | 39 | 39 | 42 | 37 |

Figure 2:
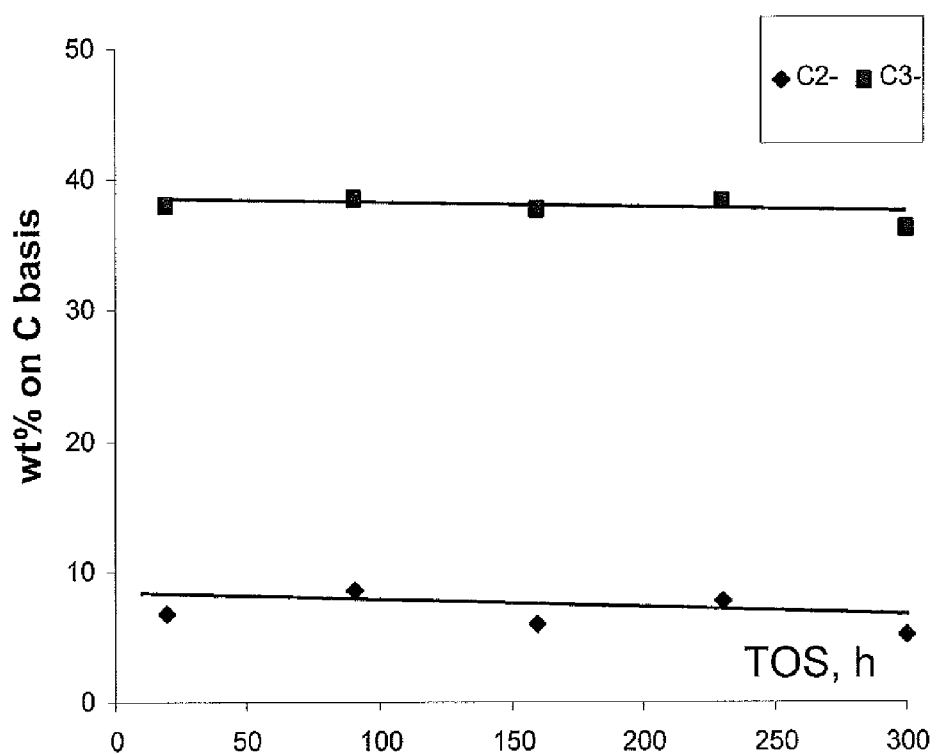
FIG. 2 depicts propylene yield in an XTO reaction as function of TOS over SAMPLE A.

FIG. 2 presents a propylene yield in XTO as function of TOS over the SAMPLE A.

Example 9-11

Catalyst tests were performed on 10 ml (~6 g) of catalyst grains (35-45 meshes) loaded in the tubular reactor. The feedstock which contains substantially non cyclic olefins C4 (~60%) was subjected to catalytic cracking in the presence of catalyst in a fixed bed reactor at 550° C., LHSV=2-10 h$^{-1}$, P=1.5 bara. The results are in table 2 and 3 hereunder. The values in table 2 and 3 are the weight percent on carbon basis. The catalytic performance is given at maximum propylene yield.

The data given below illustrate a cracking activity of the P-zeolite in C4 olefins conversion to propylene and ethylene.

TABLE 2

|  | Example 9 SAMPLE A | |
|---|---|---|
|  | Feed | Effluent* |
| Paraffins | 41.1 | 41.5 |
| Olefins | 58.8 | 55.5 |
| Dienes | 0.0 | 0.7 |
| Aromatics | 0.0 | 2.3 |
| C1 (methane) | 0.0 | 0.4 |
| Ethylene | 0.0 | 5.0 |
| Propylene | 0.3 | 20.8 |
| Butenes | 57.4 | 19.2 |

*LHSV = 2 h$^{-1}$

Figure 3:
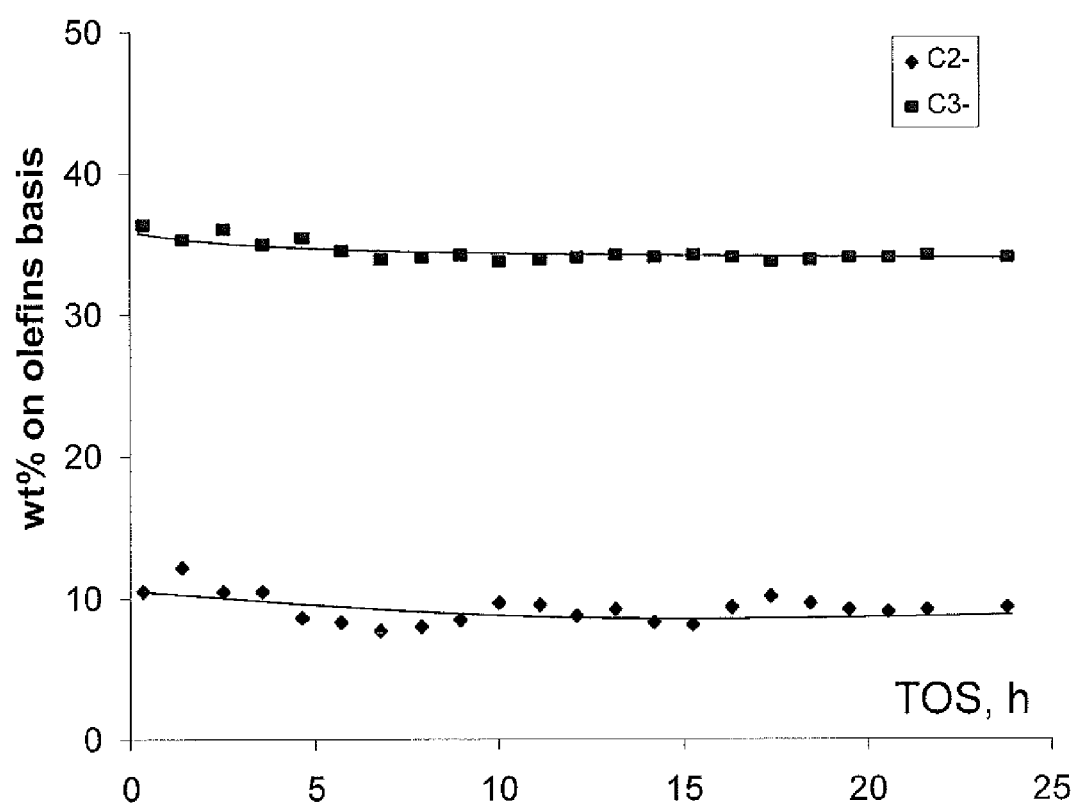
FIG. 3 depicts C2-, C3- yields on olefins basis in function on TOS in an OCP reaction.

FIG. 3 presents C2-, C3-yields on olefins basis in function on TOS in OCP.

TABLE 3

|  | Feed | Example 10 SAMPLE B Effluent** | Example 11 SAMPLE C Effluent** |
|---|---|---|---|
| Paraffins | 43.7 | 49.4 | 48.6 |
| Olefins | 56.0 | 42.8 | 48.4 |
| Dienes | 0.3 | 0.3 | 0.6 |
| Aromatics | 0.0 | 7.6 | 2.4 |
| C1 (methane) | 0.0 | 0.39 | 0.47 |
| Ethylene | 0.0 | 5.8 | 4.9 |
| Propylene | 0.1 | 17.1 | 18.0 |
| Butenes | 55.2 | 13.5 | 16.6 |

**LHSV = 10 h$^{-1}$

The invention claimed is:

1. A process of making light olefins from an oxygen containing, halogenide containing or sulphur containing organic feedstock, comprising:
    selecting a zeolite in the H$^+$ or NH$_4^+$ form that has an initial Si:Al atomic ratio of 100 or less, wherein the zeolite is an MFI or MEL;
    steaming the zeolite at a temperature ranging from 480° C. to 760° C. for 0.01-200 hours;
    after steaming, leaching the zeolite with an aqueous acid solution at conditions effective to remove a substantial part of Al from the zeolite;
    after leaching, introducing phosphorus (P) to the zeolite with an aqueous solution containing a source of P at conditions effective to introduce at least 0.05 wt % to 7 wt % of P, obtaining a first P modified zeolite;
    contacting the oxygen containing, halogenide containing, or sulphur containing organic feedstock in a first reactor with a first catalyst comprising the first P modified zeolite at conditions effective to convert at least a portion of the feedstock to form a first reactor effluent comprising light olefins and a heavy hydrocarbon fraction;
    sending the first reactor effluent to a first fractionator and separating the light olefins from the heavy hydrocarbon fraction in the first fractionator, wherein the light olefins from the first fractionator comprise ethylene and propylene, and wherein the separated light olefins are recovered;
    contacting the separated heavy hydrocarbon fraction in a second reactor with a second catalyst made from a second P modified zeolite, wherein the second P modified zeolite catalyst is the same as the first P modified zeolite catalyst, at conditions effective to convert at least a portion of the heavy hydrocarbon fraction to light olefins; and
    sending the second reactor effluent to a second fractionator and separating the light olefins from the heavy hydrocarbon fraction in the second fractionator, wherein the separated light olefins from the second fractionator comprise ethylene and propylene.

2. The process of claim 1, wherein the first P modified zeolite has been made without direct addition of an organic template, and wherein the selected zeolite is steamed with a 5 to 100% stream volume, a pressure at from 10 to 100 kPa, and in the presence of 0 to 95% of an inert gas for 0.05 to 200 hours.

3. The process of claim 1, wherein the second P modified zeolite has an initial Si:Al atomic ratio of 100 or less, and wherein the oxygen containing, halogenide containing, or sulphur containing organic feedstock that contacts the first catalyst is obtained from one or more of oil, coal, tar sand, shale, hydrocarbon residues, biomass, organic waste, natural gas, methanol, or methanol from a production of synthesis gas.

4. The process of claim 1, wherein steaming the selected zeolite dealuminates the selected zeolite, and wherein the selected zeolite has an initial Si:Al atomic ratio ranging from 4-30.

5. The process of claim 1, further comprising a step of dealumination of the second P modified zeolite by steaming, followed by a leaching step.

6. The process of claim 1, wherein the first P modified zeolite is subjected to a washing step, a drying step, or a combination thereof prior to calcining.

7. The process of claim 1, wherein the first catalyst and the second catalyst are different.

8. The process of claim 1, wherein the second P modified zeolite is made by a process comprising:
    selecting an MFI zeolite in the H$^+$ or NH$_4^+$ form that has an initial Si:Al atomic ratio of 100 or less;
    steaming the selected MFI zeolite at a temperature ranging from 480° C. to 760° C. for 0.01-200 h; and
    after steaming, leaching the selected MFI zeolite with an aqueous acid solution at conditions effective to remove an amount of Al from the selected MFI zeolite before introducing P into the selected MFI zeolite and calcining the selected MFI zeolite.

9. The process of claim 8, wherein the second P modified zeolite is subjected to a washing step, a drying step, or a combination thereof after P is added and prior to calcining.

10. The process of claim 8, wherein the light olefins are recovered from the second fractionator;
    wherein heavy hydrocarbons having 4 or more carbon atoms from the second reactor and second fractionator are recycled to the second reactor and are mixed with heavy hydrocarbons from an additional first reactor effluent that has been separated from the light olefin fraction by the first fractionator; and
    wherein the heavy hydrocarbons from the first and second fractionators are sent to the second reactor for additional processing.

11. The process of claim 8, wherein the heavy hydrocarbons from the second fractionator having 4 or more carbon atoms are sent to a third fractionator to remove and recover a heavy hydrocarbon stream comprising $C_6^+$ hydrocarbons prior to recycling a separated $C_4$-$C_5$ fraction from the third fractionator to the second reactor; and wherein separated $C_4$-$C_5$ fraction from the third fractionator is recycled with heavy hydrocarbons from an additional effluent from the first reactor that has been separated from the light olefin fraction by the first fractionator, and wherein the heavy hydrocarbons from the first and second fractionators are sent to the second reactor for additional proceeding.

12. The process of claim 10, wherein in order to adjust a propylene to ethylene production ratio for the process, ethylene is recycled to the second reactor; and wherein the recycled ethylene is from a source selected from the first fractionator, the second fractionator, from both the first fractionator and the second fractionator, or from a common recovery section.

13. The process of claim 10, wherein in order to adjust a propylene to ethylene ratio for the process, ethylene is recycled to the first reactor; and wherein the recycled ethylene is from a source selected from the first fractionator, the second fractionator, from both the first fractionator and the second fractionator, or from a common recovery section.

14. The process of claim 8, wherein the oxygen containing, halogenide containing, or sulphur containing organic feedstock is obtained from one or more of oil, coal, tar sand, shale, hydrocarbon residues, biomass, organic waste, natural gas, methanol, or methanol from a production of synthesis gas, and wherein the produced and separated ethylene is further polymerized with one or more comonomers.

15. The process of claim 8, wherein the oxygen containing, halogenide containing, or sulphur containing organic feedstock is obtained from one or more of oil, coal, tar sand, shale, hydrocarbon residues, biomass, organic waste, natural gas, methanol, or methanol from a production of synthesis gas, and wherein the produced and separated propylene is further polymerized with one or more comonomers.

16. A process of making light olefins from an oxygen containing, halogenide containing, sulphur containing organic feedstock, comprising:

selecting a zeolite in the $H^+$ or $NH_4^+$ form that has an initial Si:Al atomic ratio of 100 or less, wherein the zeolite is MFI or MEL;

steaming the zeolite at a temperature ranging from 480° C. to 760° C. for 0.01-200 hours:

after steaming, leaching the zeolite with an aqueous acid solution at conditions effective to remove a substantial part of Al from the zeolite;

after leaching, introducing phosphorus (P) to the zeolite with an aqueous solution containing a source of P at conditions effective to introduce at least 0.05 wt % to 7 wt % of P, obtaining a first P modified zeolite;

contacting the oxygen containing, halogenide containing, or sulphur containing organic feedstock in a XTO reactor having an inlet temperature of from 540° C. to 580° C. and an olefin partial pressure of from 0.1 to 2 bars with the first P modified zeolite conditions effective to convert at least a portion of the feedstock to form a XTO reactor effluent comprising light olefins and a heavy hydrocarbon fraction;

sending the XTO reactor effluent to a first fractionator and separating the light olefins from the heavy hydrocarbon fraction in the first fractionator, wherein the light olefins from the first fractionator comprise ethylene and propylene, and wherein the separated light olefins are recovered;

contacting the separated heavy hydrocarbon fraction in an OCP reactor having an inlet temperature of from 540° C. to 590° C., and olefin partial pressure of from 0.1 to 2 bars, and a LHSV of from 1 to 30 hr $^{-1}$, with a second P modified zeolite, wherein the second P modified zeolite catalyst is the same as the first P modified zeolite catalyst, at conditions effective to convert at least a portion of the heavy hydrocarbon fraction to light olefins; and sending the OCP reactor effluent to a second fractionator and separating the light olefins from the heavy hydrocarbon fraction in the second fractionator, wherein the separated light olefins from the second fractionator comprise ethylene and propylene.

17. The process of claim 16, wherein the light olefins are recovered from the second fractionator;

wherein heavy hydrocarbons having 4 or more carbon atoms from the OCP reactor and second fractionator are recycled along with heavy hydrocarbons from an additional effluent from the XTO reactor that has been separated from the light olefin fraction by the first fractionator; and wherein the heavy hydrocarbons from the XTO reactor and second fractionator are sent to the OCP reactor for additional processing.

18. The process of claim 16, wherein the light olefins are recovered from the second fractionator;

wherein the heavy hydrocarbons having 4 or more carbon atoms from the second fractionator are sent to a third fractionator to remove a heavy hydrocarbon stream comprising $C_6^+$ hydrocarbons prior to recycling a separated $C_4$-$C_5$ fraction from the third fractionator to the OCP reactor;

wherein $C_4$-$C_5$ fraction from the third fractionator is recycled with heavy hydrocarbons from an additional effluent from the XTO reactor that has been separated from the light olefin fraction by the first fractionator, and wherein the heavy hydrocarbons from the first and third fractionators are sent to the OCP reactor for additional processing; and wherein the second P modified zeolite has an initial Si:Al atomic ratio of 100 or less.

19. The process of claim 1, wherein the first catalyst and the second catalyst are the same.

20. The process of claim 1, wherein the aqueous acid solution comprises:

an organic acid selected from a group consisting of citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid, trifluoroacetic acid, a salt thereof, or combinations thereof; or an inorganic acid selected from a group consisting of nitric acid, hydrochloric acid, methansulfuric acid, phosphoric acid, phosphonic acid, sulfuric acid, a salt thereof, or combinations thereof.

21. The process of claim 1, wherein the selected zeolite is an MFI.

22. The process of claim 1, wherein the selected zeolite is an MEL.

* * * * *